(12) United States Patent
Soreide

(10) Patent No.: US 9,498,002 B1
(45) Date of Patent: Nov. 22, 2016

(54) MULTI-CHAMBER VAPORIZER

(71) Applicant: REVOLVER PEN, LLC, Pompano Beach, FL (US)

(72) Inventor: Lars Kristian Soreide, Pompano Beach, FL (US)

(73) Assignee: REVOLVER PEN, LLC, Pompano Beach, FL (US)

( * ) Notice: Subject to any disclaimer, the term of this patent is extended or adjusted under 35 U.S.C. 154(b) by 0 days.

(21) Appl. No.: 14/858,121

(22) Filed: Sep. 18, 2015

(51) Int. Cl.
*F24F 3/14* (2006.01)
*A61H 33/12* (2006.01)
*A24F 47/00* (2006.01)
*A61M 11/04* (2006.01)
*A61M 15/06* (2006.01)

(52) U.S. Cl.
CPC ........... *A24F 47/008* (2013.01); *A61M 11/041* (2013.01); *A61M 15/06* (2013.01)

(58) Field of Classification Search
None
See application file for complete search history.

(56) References Cited

U.S. PATENT DOCUMENTS

| | | | | |
|---|---|---|---|---|
| 3,410,488 A * | 11/1968 | Sugimura | ............. | B05B 7/2429 239/326 |
| 4,603,030 A * | 7/1986 | McCarthy | ............... | A61L 9/122 239/60 |
| 4,629,604 A * | 12/1986 | Spector | ............... | A01M 1/2077 261/DIG. 88 |
| 5,133,042 A * | 7/1992 | Pelonis | ...................... | F24F 1/02 261/DIG. 65 |
| 5,167,877 A * | 12/1992 | Pai | ........................ | A61L 9/122 261/18.1 |
| 5,805,768 A * | 9/1998 | Schwartz | .......... | A61M 15/0045 261/DIG. 65 |
| D459,950 S * | 7/2002 | Bush | .......................... | D7/553.6 |
| 6,581,915 B2 * | 6/2003 | Bartsch | ............... | A01M 1/2033 261/104 |
| 6,713,024 B1 * | 3/2004 | Arnell | ..................... | A61L 9/125 239/57 |
| 7,011,795 B2 * | 3/2006 | Thompson | .............. | A61L 9/035 222/167 |
| 7,203,417 B2 * | 4/2007 | Manne | .................... | A61L 9/035 392/390 |
| 7,376,344 B2 * | 5/2008 | Manne | .................... | A61L 9/035 392/390 |
| 7,610,118 B2 * | 10/2009 | Schramm | ........... | A01M 1/2033 239/69 |
| 7,691,336 B2 * | 4/2010 | Westring | ............. | A01M 1/2033 261/26 |
| 7,734,159 B2 * | 6/2010 | Beland | .................... | A61L 9/035 392/390 |
| 8,170,405 B2 * | 5/2012 | Harris | ................. | A01M 1/2033 392/386 |
| 8,385,730 B2 * | 2/2013 | Bushman | ................. | A61L 9/03 392/386 |
| 8,414,834 B2 * | 4/2013 | Gorman | ................. | A47G 33/06 422/120 |
| 8,469,293 B2 * | 6/2013 | Doty | ....................... | A61L 9/122 239/44 |
| 9,265,853 B2 * | 2/2016 | Scott | ....................... | A61L 9/122 |
| 2005/0117895 A1 * | 6/2005 | Balch | ................... | A61M 11/041 392/386 |
| 2006/0196968 A1 * | 9/2006 | Rabin | ................... | A61M 15/00 239/136 |
| 2011/0030706 A1 * | 2/2011 | Gibson | ................ | A61M 11/041 131/328 |
| 2011/0210458 A1 * | 9/2011 | Brodbeck | ......... | A61M 16/1075 261/128 |
| 2012/0219274 A1 * | 8/2012 | Curran, Jr. | ................ | A61L 9/03 392/386 |
| 2015/0125136 A1 * | 5/2015 | Sanchez | .................... | A61L 9/03 392/394 |

* cited by examiner

*Primary Examiner* — Thor Campbell
(74) *Attorney, Agent, or Firm* — The Concept Law Group, P.A.; Scott D. Smiley; Yongae Jun

(57) ABSTRACT

A multi-chamber vaporizer is disclosed. The vaporizer includes a heating assembly with a heating element, the heating element having a portion thermally coupled to an airflow passage. A plurality of herbal placement chambers is rotatable relative to the airflow passage. Further, a track assembly having an herbal support surface extends about a central axis at a track radius and with a motor operably configured to rotate the herbal support surface about the central axis at a rotation rate. The herbal support surface is operably configured to support the herbal placement chambers thereon for rotation about the central axis to the airflow passage.

18 Claims, 6 Drawing Sheets

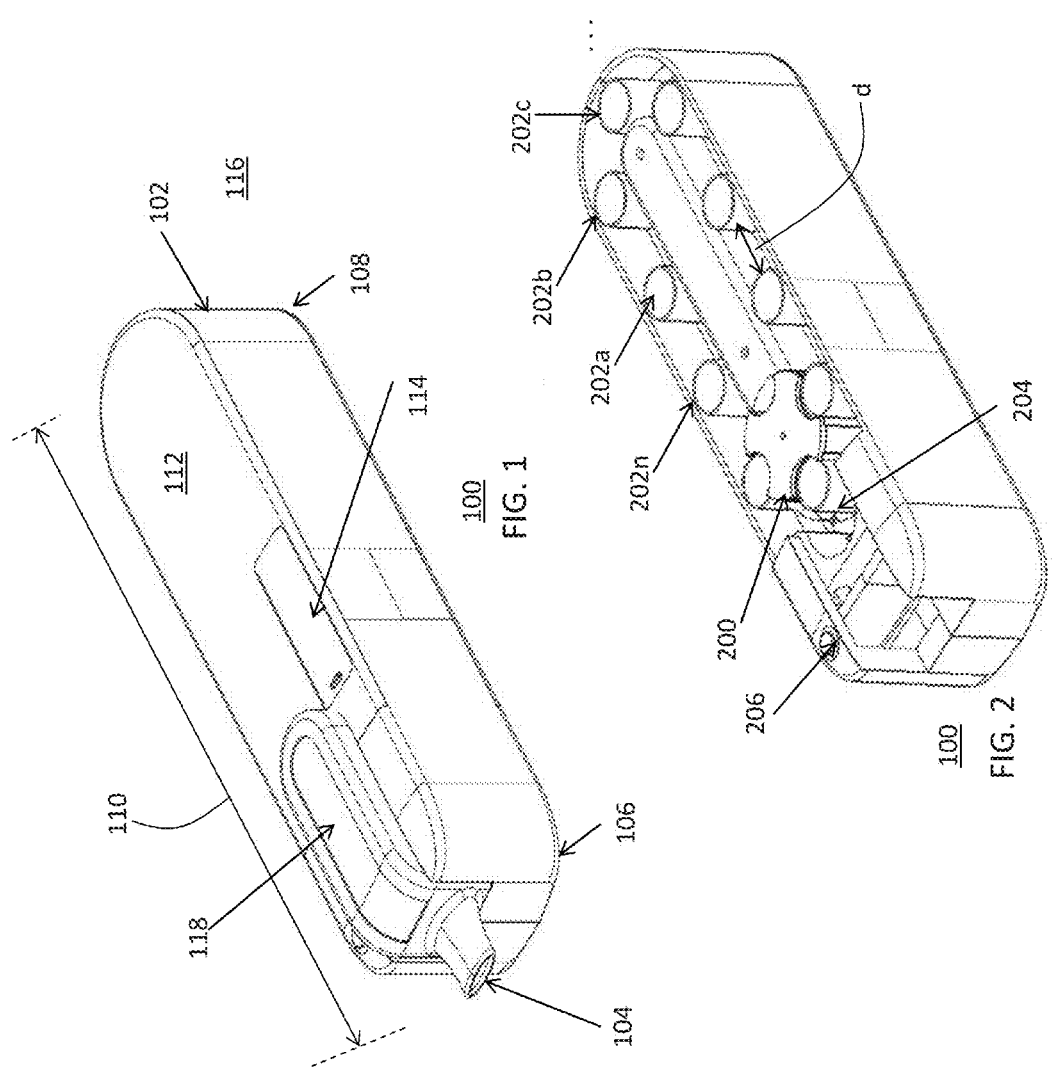

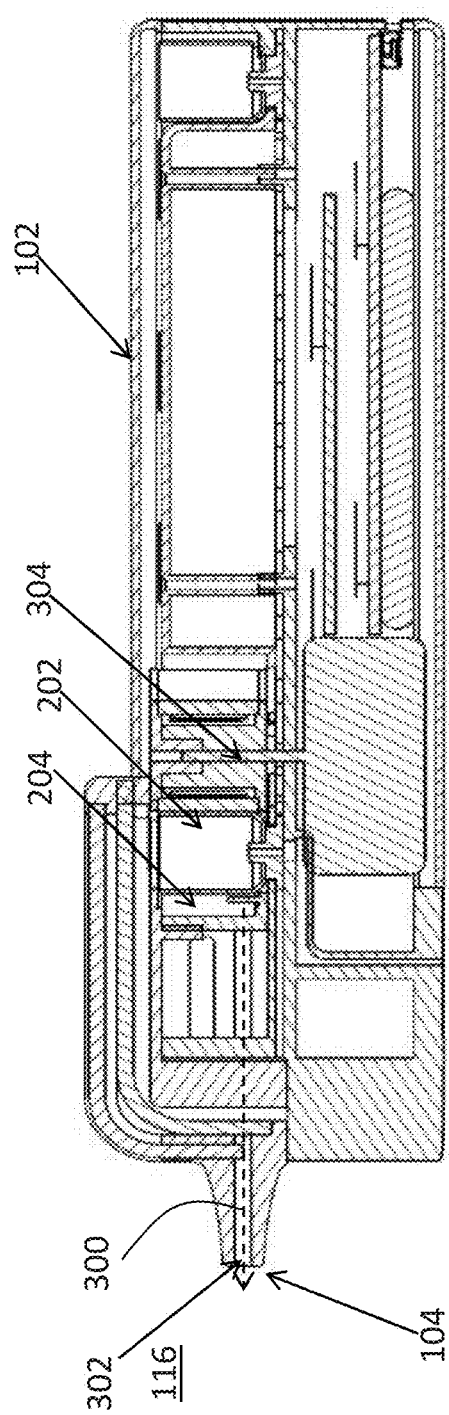

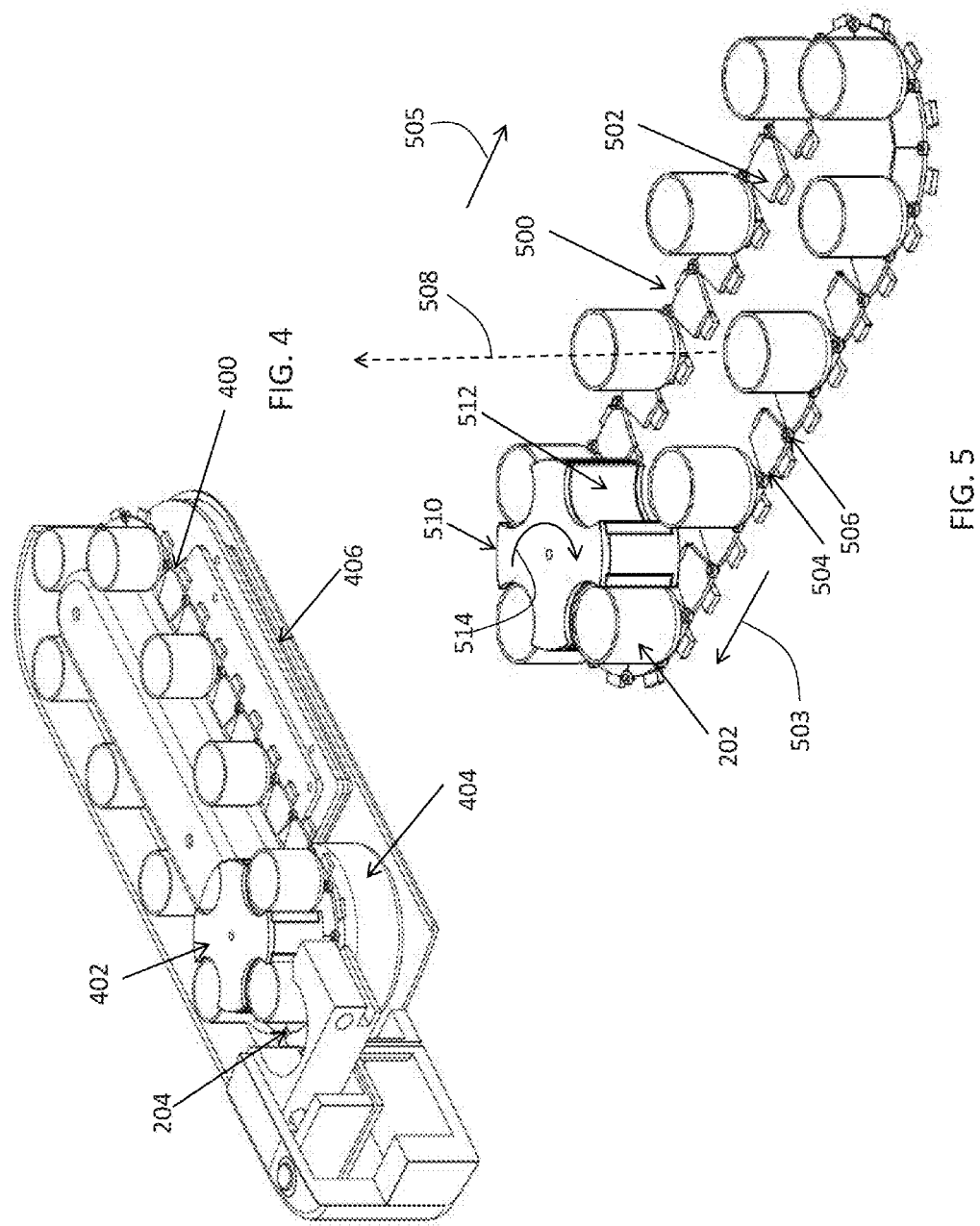

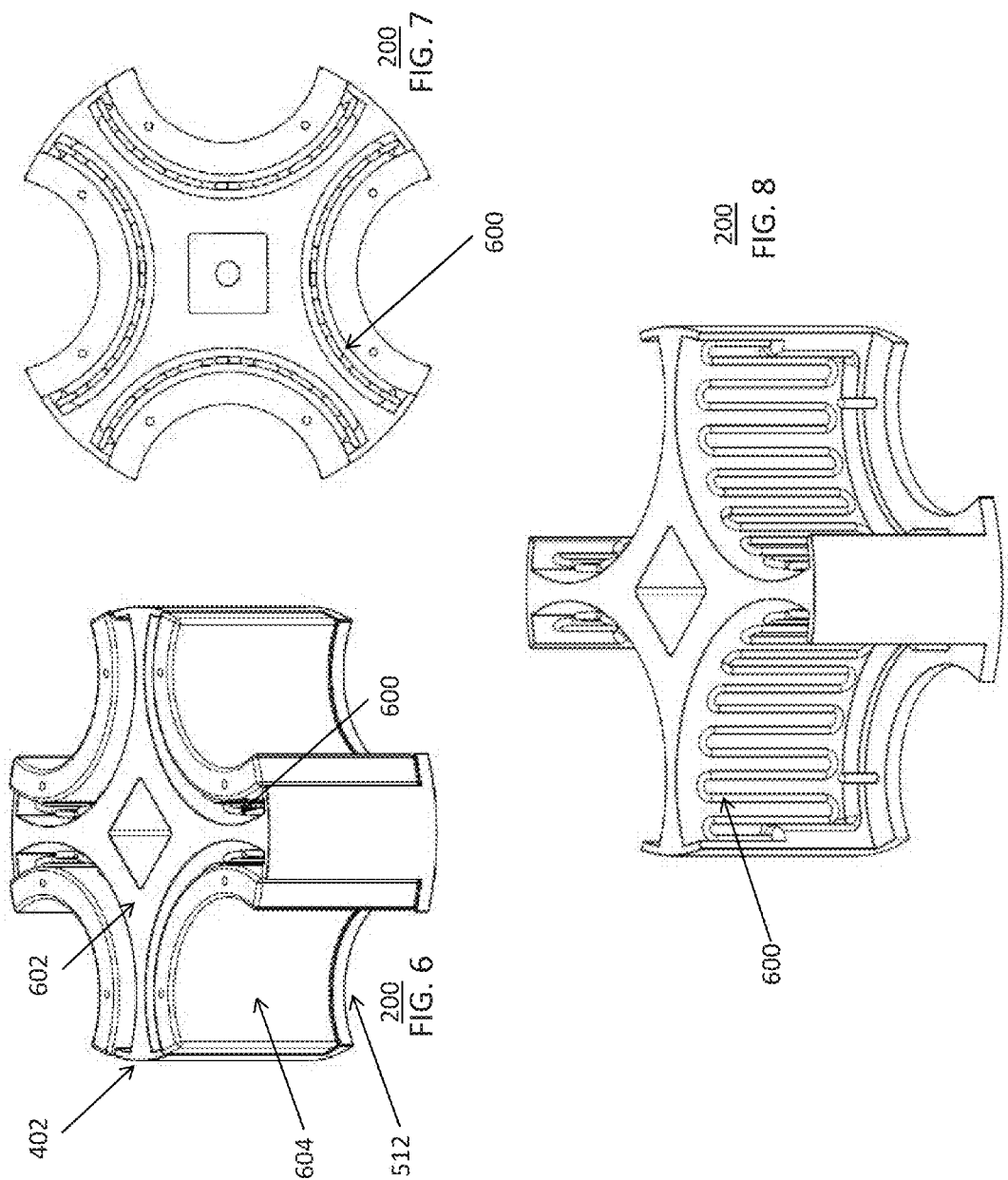

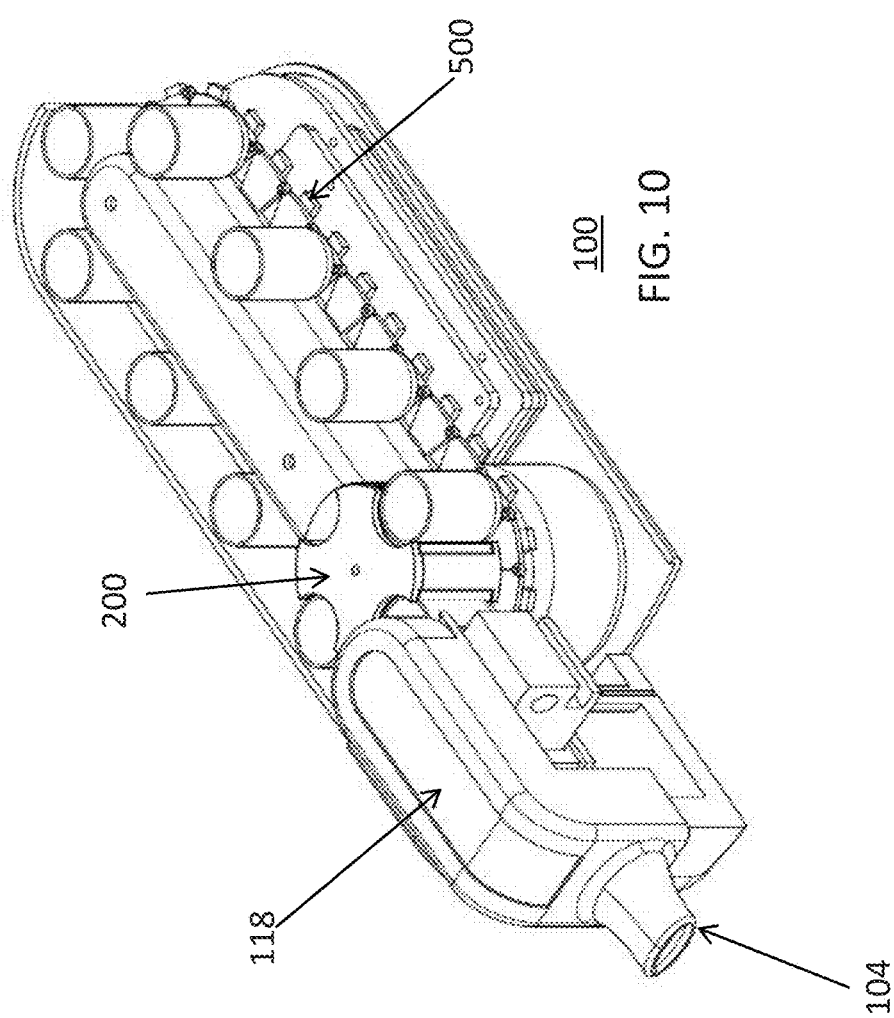

MULTI-CHAMBER VAPORIZER

FIELD OF THE INVENTION

The present invention relates generally to vaporizers, and more particularly relates to a multi-chamber vaporizer assembly.

BACKGROUND OF THE INVENTION

A vaporizer is a device used to extract the active ingredients of plant material, e.g., tobacco, or other herbs or blends, for inhalation by a human. Another type of vaporizer is an e-cigarette that typically heats a liquid solution into vapors. Vaporization involves heating a material, either by conduction or by convection, so that its active compounds boil off into a vapor. As opposed to smoking, vaporization is said to avoid the production of irritating, toxic, and carcinogenic by-products. Studies show that vapor contains substantially zero particulate matter or tar, and, in comparison to smoking, significantly lower concentrations of noxious gases such as carbon monoxide. It has also been shown that, in comparison to other drug delivery methods, such as ingestion, vaporization has a more rapid onset of pharmacological effect, direct delivery into the bloodstream (via the lungs), and more precise titration such that the desired level is reached and not exceeded, enabling consistent and appropriate dosage.

Prior art vaporizers typically include only a single loading area into which substances (e.g., tobacco, e-cigarette liquid, etc.) may be loaded for vaporizing. Many users prefer the use of a portable vaporizer that can be used on the go and carried with the user at all times on their person. Because portable vaporizers have only a single loading area, when the vaporizer requires a refill in order to be utilized the user is required to retrieve an additional amount of the vaporizable substance and load that substance into the singular loading area. This can be a cumbersome and time-consuming task. In addition, there is a social stigma that is often associated with the use of such vaporizers. The user may not desire others to see him/her loading the substance into the vaporizer. Also, the user may not have the substance on hand to refill the vaporizer and therefore has missed out on an opportunity to enjoy the vaporizing experience. Unfortunately, existing vaporizers do not provide for a portable vaporizer that allows users to "refill" the vaporizer in a public environment quickly, easily, and discretely.

Therefore, a need exists to overcome the problems with the prior art as discussed above.

SUMMARY OF THE INVENTION

The invention provides a rotatable multi-chamber vaporizer that overcomes the hereinafore-mentioned disadvantages of the heretofore-known devices and methods of this general type.

With the foregoing and other objects in view, there is provided, in accordance with the invention, a vaporizer having a housing substantially enclosing a heating assembly with a heating element and a plurality of vaporizable substance receptacles therein, the heating element having a portion thermally coupled to an airflow passage; and an actuator, at least a portion of the actuator disposed on a surface of the housing and the actuator operably configured to cause at least one of the plurality of vaporizable substance receptacles to move from a first position to a second position for vaporization.

In accordance with another embodiment of the present invention, the plurality of vaporizable substance receptacles is rotatable along a circular path defined by a central axis.

In accordance with yet another feature, an embodiment of the present invention includes a track having a vaporizable substance receptacle support surface extending about the central axis, wherein each of the plurality of vaporizable substance receptacles are disposed a separation distance from one another and are supported in an upright position by the vaporizable substance receptacle support surface.

In accordance with yet another feature, an embodiment of the present invention includes a motor operably configured to rotate the plurality of vaporizable substance receptacles about a central axis at a rotation rate.

In accordance with yet another feature of the present invention, the housing is shaped to fit substantially within a standard-sized clothing pocket.

In accordance with another feature, an embodiment of the present invention includes a motor operably configured to selectively move the plurality of vaporizable substance receptacles.

In accordance with a further feature of the present invention, the heating element and the plurality of vaporizable substance receptacles are operably configured to rotate together.

In accordance with yet a further feature, an embodiment of the present invention includes a rotating gear operably configured to physically engage at least one of the plurality of vaporizable substance receptacles to rotate said vaporizable substance receptacle about a central axis.

In accordance with another feature, an embodiment of the present invention includes an output conduit defining the airflow passage and placing the airflow passage in fluid communication with an outside environment, the output conduit having a transparent window through which at least one of the plurality of vaporizable substance receptacles is visible from the outside environment.

In accordance with another feature of the present invention, each of the plurality of vaporizable substance receptacles are disposed a separation distance from one another.

In accordance with yet another feature of the present invention, a portable hand-held vaporizer includes a heating assembly with a heating element, the heating element having a portion thermally coupled to an airflow passage; at least two vaporizable substance receptacles; a motor; and a rotation assembly having a support surface extending about a central axis, the motor operably configured to rotate the support surface about the central axis at a rotation rate and the support surface supporting the at least two vaporizable substance receptacles thereon for rotation about the central axis.

In accordance with another feature of the present invention, the at least two vaporizable substance receptacles are of a conductive material.

In accordance with yet another feature, an embodiment of the present invention includes an actuator communicatively coupled to the motor and operably configured to allow a user to selectively cause the rotation assembly to rotate about the central axis.

In accordance with another feature of the present invention includes a rotating gear configured to physically engage the at least two vaporizable substance receptacles to rotate said vaporizable substance receptacles about the central axis.

In accordance with another feature, an embodiment of the present invention includes a portable vaporizer having a heating assembly with a heating element, the heating element having a portion thermally coupled to an airflow passage; a plurality of vaporizable substance receptacles; and an actuator operably configured to cause at least one of the plurality of vaporizable substance receptacles to move from a first position to a second position for vaporization.

In accordance with yet another feature, an embodiment of the present invention also includes a motor; and a track having a support surface extending about a central axis, the plurality of vaporizable substance receptacles disposed on the support surface and the motor operably configured to rotate the support surface.

Although the invention is illustrated and described herein as embodied in a rotatable multi-chamber vaporizer, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the housing of the vaporizer. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 1 is a downward-looking perspective view of a rotatable multi-chamber vaporizer in accordance with an embodiment of the present invention;

FIG. 2 is a fragmentary, downward-looking perspective view of the vaporizer of FIG. 1, shown without a top cover or a mouthpiece, in accordance with the present invention;

FIG. 3 is a cross-sectional view of the vaporizer of FIG. 1, in accordance with the present invention;

FIG. 4 is a fragmentary, downward-looking perspective view of the vaporizer of FIG. 1, shown without the top cover, the mouthpiece, and one of the sidewalls, in accordance with the present invention;

FIG. 5 is a downward-looking perspective view of rotatable heating and track assemblies of the vaporizer of FIG. 1, in accordance with the present invention;

FIG. 6 is a downward-looking perspective view of the heating assembly of the vaporizer of FIG. 1, in accordance with the present invention;

FIG. 7 is a plan view of the heating assembly of the vaporizer of FIG. 1, in accordance with the present invention;

FIG. 8 is a fragmentary, downward-looking perspective view of the heating assembly of FIG. 10, shown without some of the sidewalls so that the heating elements are viewable, in accordance with the present invention;

FIG. 10 is a fragmentary, downward-looking perspective view of the vaporizer of FIG. 1, shown without the top cover and one of the sidewalls, in accordance with the present invention.

DETAILED DESCRIPTION

Figure 9:
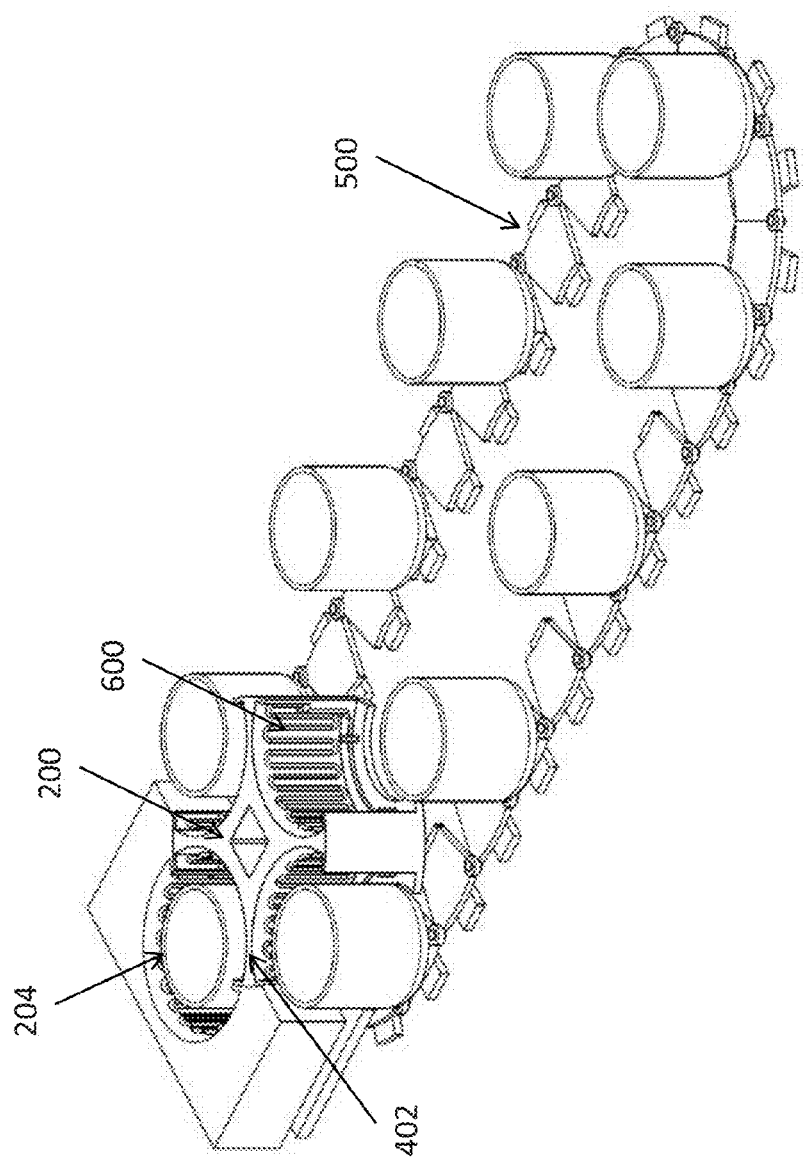
FIG. 9 is a fragmentary, downward-looking perspective view of the rotatable heating and track assemblies of the vaporizer of FIG. 1, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient rotatable multi-chamber vaporizer. Embodiments of the invention provide for a heating assembly that includes a selectively rotatable track that supports multiple independent chambers for storing a vaporizable substance therein (i.e., a vaporizable substance receptacle). In addition, embodiments of the invention provide for a gear that rotates the track so that each of the vaporizable substance receptacles can rotate into the heating chamber. In some embodiments, the gear also supports a plurality of conductive heating elements thereon to form the heating chamber. In a further embodiment, when the substance within the actively heated chamber is vaporized and the user desires to continue vaporizing, the user may engage an actuator that rotates the track and gear assembly so that the next vaporizable substance receptacle is rotated into the heating chamber for vaporizing. In yet a further embodiment, the mouthpiece may be configured as the actuator such that movement of the mouthpiece activates a motor that rotates the gear and track system. Embodiments of the invention also provide for transparent windows that allow a user to view rotation of the vaporizable substance receptacles within the vaporizer and also to view the heating assembly, as the active substance is boiled off into a cloud of vapors within the vaporizer housing.

Referring now to FIG. 1, one embodiment of the present invention is shown in a downward-looking perspective view. FIG. 1 shows several advantageous features of the present invention, but, as will be described below, the invention can be provided in several shapes, sizes, combinations of features and components, and varying numbers and functions of the components. The first example of a portable vaporizer 100, as shown in FIG. 1, includes a housing 102 and an output conduit 104. At first glance, the shape of the housing 102 and the output conduit 104 can be readily appreciated to be much more discrete and compact than that of prior-art vaporizers generally known in the art. In some embodiments, the housing 102 is generally shaped to fit within a standard-sized clothing pocket so it can be easily transportable and not readily identifiable by the viewing public.

The housing 102 includes a first end 106 and a second end 108, opposite to the first end 106, separated by a housing length 110. In one embodiment, the housing length 110 is at most approximately 6 inches to allow the portable vaporizer 100 to fit within a standard-sized clothing pocket and be transportable. In other embodiments, the housing length 110 is greater than 6 inches, but sufficiently sized to be fitted within a standard-sized clothing, e.g., pants, pocket. In one embodiment, the housing 102 and the output conduit 104 can be seen as having a shape as a pen. The housing 102 may also have a cover 112 which protects the inside of the housing 102 and components substantially enclosed within the housing 102 so as to be concealed therein from the viewing public. As used herein, the term "substantially enclosed" is intended to indicate an enclosure that may or may not include one or more nominal openings.

In one embodiment, the housing 102 is made completely from an outer shell of durable plastic. In other embodiments, the housing 102 has portions made of plastic or other heat resistant materials so that the user is able to comfortably grip the housing 102 without his or her fingers without feeling uncomfortably high temperatures. In another embodiment, some portions of the housing 102 may be made from metallic or other conductive materials. In yet further embodiments, the entire housing 102, or portions thereof, may be made from a metallic, composite, ceramic, or other material or any of the above combinations.

Referring now to FIG. 2, with reference to FIG. 1, a heating assembly 200 and a plurality of vaporizable substance receptacles 202*a-n* is shown in a fragmentary, downward-looking perspective view of the portable vaporizer 100, shown without the cover 112 or the mouthpiece 104 so that a portion of the internal components are viewable. When assembled, the heating assembly 200 and the plurality of vaporizable substance receptacles 202*a-n* are substantially enclosed by the housing 102, where the number of vaporizable substance receptacles 202*a-n* between "a" and "n" can be any number. The heating assembly 200 defines a heating chamber 204 that actively heats the vaporizable substance receptacle 202 that is disposed within the heating chamber 204 so that the vaporizable substance therein (e.g., tobacco, e-cigarette liquid, etc.) can be vaporized. The "vaporizable substance receptacle" is defined as a container intended to hold a substance to be vaporized. In one embodiment, the vaporizable substance receptacle 202 is made of a thermally conductive material that has the ability to transfer heat across the material at a generally high rate, such as a metallic material. In another embodiment, the vaporizable substance receptacle 202 is made of other materials, such as a composite, ceramic, or the like. Providing the vaporizable substance receptacle 202 as a thermally conductive material is preferable in some embodiments so that the vaporizable substance therein may be more easily heated when actively heated by the heating chamber 204. In one embodiment, the vaporizable substance receptacle 202 includes one or more apertures so that the vapors produced by the heat can travel from the vaporizable substance receptacle 202 into the output conduit 104 and into the user's mouth. Preferably, the one or more apertures is sized and shaped so as to allow air to enter and/or exit the vaporizable substance receptacle 202, but also resists any herb, or debris from the herbs, or other materials from entering an airflow passage that that is intended to transport heated air into the user's mouth. In a further embodiment, the vaporizable substance receptacle 202 may be formed as a mesh container or another air permeable container. In yet another embodiment, the vaporizable substance receptacle 202 is formed as a loadable cartridge or pod that is air permeable. The heating assembly 200 will be described in more detail herein below, with reference to FIGS. 6-8.

In one embodiment, the cover 112 may be formed as a selectively removable cover 112, similar to a cell phone back cover, which can be snapped on or easily unsnapped and slid off to reveal at least a portion of the components within the housing 102. In one embodiment, the cover 112 is configured to frictionally fit over the remainder of the housing 102 walls, as shown in FIG. 1. In another embodiment, the cover 112 is formed as a pivoting door. In such an embodiment, the cover 112 may include a hinge connector and allow a user to hingedly open and close the cover 112 for selective access to the plurality of vaporizable substance receptacles 202*a-n*. This feature allows users full physical access to each of a plurality of vaporizable substance receptacles 202*a-n* within the housing 102 so that all of the receptacles 202*a-n* may be filled with the vaporizable substance during one instance. Alternatively, users may fill only a portion of the receptacles 202 (e.g., three out of six total chambers) within the housing 102 via a loading window 114. The loading window 114 may include a transparent panel (e.g., glass material) that may be selectively closed and opened in order to provide the user with access to the portion of the receptacles 202 for loading purposes. In one embodiment, the loading window 114 may be sized and shaped to allow physical access to at least two of the receptacles 202 for refilling with a vaporizable substance from outside of the housing 102. In another embodiment, the loading window 114 may be sized and shaped to allow two of the receptacles 202 to be filled with a vaporizable substance from outside of the housing 102. In this embodiment, the loading window 114 includes a length and a width sized so that two neighboring receptacles 202, which may be separated by a separation distance, d, are viewable through the transparent loading window 114. Accordingly, physical access to the two receptacles 202 via the loading window 114 is provided to the user when the loading window 114 is open. In other embodiments, the loading window 114 may be other sizes and shapes. The loading window 114 is preferably transparent or semi-transparent in some embodiments, but may be opaque in other embodiments. In one embodiment, the loading window 114 may be configured to selectively slide open and closed. In another embodiment, the loading window 114 may be configured to pivotally open and close. Advantageously, transparent embodiments of the loading window 114 provide a benefit that the user may be able to view rotation of the receptacles 202 from the outside environment 116. The term "outside environment" is intended to indicate an environment external to the vaporizer 100. Some users will enjoy the ability to see the moving components within the vaporizer 100.

In one embodiment, the output conduit 104 is physically coupled to the first end 106 of the housing 102. The output conduit 104 can be considered an air sealed output conduit. The output conduit 104 is shaped to conform to the user's mouth and can be considered a mouth piece. In one embodiment, the output conduit 104 is made of a non-conductive material so that the user can safely place his or her mouth on the mouthpiece to create a "suction effect" and inhale the generated vapors. Referring briefly to FIG. 3, in use, after the vaporizable substance reaches the desired temperature, the user places his or her mouth over the output conduit 104 and inhales, which pulls heated air from the heating chamber 204 through an airflow passage 300 defined by the output conduit 104. The heated air travels through the airflow passage 300 and out through an opening 302 of the output conduit 104 into the outside environment 116. Stated another way, the output conduit 104 places the airflow passage 300 in fluid communication with the outside environment 116, allowing vapors from the actively heated receptacle 202 to travel along the airflow passage 300 and into the outside environment 116. As used herein, the term "actively heated" is intended to indicate the vaporizable substance receptacle 202 that is disposed within the heating chamber 204, as opposed to other receptacles 202 within the housing 102 that may experience some nominal heating due to a relative proximity to the heating chamber 204.

Referring again primarily to FIGS. 1-2, in one embodiment, the output conduit 104 includes a vapor viewing window 118. The vapor viewing window 118 is preferably made of a transparent material, such as glass, or a transparent plastic or polymer-based material. The vapor viewing window 118 may be disposed on the housing 102 so that at least a portion of the heating assembly 200 is visible from the outside environment 116. In one embodiment, the vapor viewing window 118 is disposed directly above the heating chamber 204 so that the user is able to view the creation and movement of the vapors from the heating chamber 204 toward the airflow passage 300 (see FIG. 3). It is believed that many users would find the visual experience enjoyable.

Referring to FIGS. 4 and 5, one embodiment of a rotation assembly 400 is described in fragmentary, downward-looking perspective views. The exemplary rotation assembly 400 includes a track structure 500. However, it is understood that there are multiple variations or configurations of the rotation assembly 400, with and without a track, which are within the spirit and scope of this invention.

In one embodiment, the track structure 500 includes a support surface 502. In a further embodiment, the support surface 502 is defined by an upper, exterior surface of the track structure 500. In yet a further embodiment, the support surface 502 is formed as a plurality of support segments 504 that may be pivotally connected to one another in an edge-to-edge formation via, for example, a pivot pin 506. The support segments 504 may be shaped as a trapezoid such that where the track structure 500 is curved, edges of neighboring support segments 504 are able to engage one another without vertical overlapping. In other embodiments, the support segments 504 may be formed as other polygonal shapes, or may be formed as other non-polygon shapes and sizes. In one embodiment, the support surface 502 may be configured to support the plurality of vaporizable substance receptacles 202 thereon. In another embodiment, the plurality of vaporizable substance receptacles 202 are supported in an upright position on the support surface 502. In yet another embodiment, the vaporizable substance receptacles 202 may be secured to the track structure 500 by an adhesive material, a mechanical fastener, gravitational forces, frictional forces, or the like. In one embodiment, the track structure 500 is made of plastic or other polymer-based material. In another embodiment, the track structure 500 is made of a metallic or other conductive material. In a further embodiment, the track structure 500 may be made of other materials or composites.

In one embodiment, the track structure 500 extends about an imaginary vertical axis 508 defined as a central axis 508 about which the support surface 502 rotates. In another embodiment, the central axis 508 can be considered a fixed axis that does not change its orientation during rotation. In a further embodiment, the track structure 500 extends about the central axis 508 in a circular rotational pathway. In another embodiment, the track structure 500 may be provided in other non-circular shapes and configurations. The support surface 502 of the track structure 500 physically supports the plurality of vaporizable substance receptacles 202 thereon, such that rotation of the track structure 500 causes the receptacles 202 to rotate, as well, so that a receptacle 202 with a substance that has already been vaporized can be rotated out or otherwise moved and the next receptacle 202, with an unvaporized substance, can be loaded into the heating chamber 204 for vaporization. Stated another way, the plurality of vaporizable substance receptacles 202 may be selectively moveable such that at least one of the receptacles 202 is moved in a first direction 503 towards the airflow passage 300 (see FIG. 3) and into the heating chamber 204 for actively heating the substance therein. At the same time, another one of the receptacles 202 is moved in a second direction 505 away from the airflow passage 300 (see FIG. 3) and outside of the heating chamber 204 so that it is no longer actively heated by the heating chamber 204. The first direction 503 may be opposite the second direction 505.

In one embodiment, in addition to the track structure 500, the rotation assembly 400 also includes a gear 402, a motor 404, a controller 406, and a switch (not shown), communicatively coupled to one another for implementing rotation of the vaporizable substance receptacles 202.

The gear 402 can be considered a rotational gear 402. In one embodiment, the gear 402 defines a plurality of cogs 510 or teeth. The region between each of the plurality of cogs 510 defines a receiving area 512 sized and shaped to receive a receptacle 202 therein. The exemplary embodiment depicts four cogs 510. However, it is understood that in some embodiments there may be more than four cogs 510 or less than four cogs 510. The cogs 510 and mating receptacles 202 can be likened, in operation, to two meshing gears transmitting rotational motion from one to the other in or to rotate the track structure 500. Stated another way, the gear 402 is configured to physically engage the vaporizable substance receptacles 202 to rotate said receptacles about the central axis 508 at a track rotation rate. In one embodiment, the motor 404 is operably configured to rotate the support surface 502 of the track structure 500 about the central axis 508 at the track rotation rate. The motor 404 may be physically coupled to the gear 402 via, for example, a shaft 304 (see FIG. 3). As the motor 404 rotates, the shaft 304 is rotated, as well, causing the gear 402 to rotate. Rotational forces 514 are transmitted from the gear 402 to the track structure 500 in order to cause the track structure 500 to rotate. More particularly, the gear 402 causes the receptacles 202 to rotate, which, in turn rotates the track structure 500.

In one embodiment, the motor 404 may be a DC motor. In another embodiment, the motor 404 may be an AC motor. In addition, the motor 404 may be configured to rotate in a clockwise direction in one embodiment, and/or a counter-clockwise direction in another embodiment. The motor 404 may be configured to rotate at a variety of rotational speeds. There are many types of existing motors that may be used with the present invention. Preferably, the motor includes a relatively small form factor to be able to be substantially enclosed by the housing 102 (not shown), which may also be sized and shaped to fit within a standard-sized clothing pocket, as explained above. In one embodiment, the motor 404 and the controller 406 may be powered by a rechargeable or non-rechargeable battery.

In one embodiment, the controller 406 provides the circuitry to control operation and rotational movement within the vaporizer 100. More particularly, the controller 406 may be communicatively coupled to the motor 404 and the switch (not shown) for receiving and transmitting control signals thereto. In one embodiment, the switch is an electronic circuit component that activates rotation of the motor 404. As is known in the art, a switch may be considered an electromechanical device with two or more electrical terminals that may be used to represent an on or an off condition. In one embodiment, when the two or more electrical terminals contact one another, current may flow through, which provides a control signal to the controller 406. Alternatively, the electrical terminals may be connected together by default and interruption of the connection may cause the controller 406 to perform a desired response. Many known switches may be used with the present invention including but not limited to a slide switch, toggle switch, rotary switch, rocker switch, push button switch, and the like. In the exemplary embodiment, the switch is coupled to the output conduit 104 (see FIG. 3) and the output conduit 104 can be considered an actuator. As used herein, the term "actuator" is defined as a mechanical or electromechanical device for moving or controlling something. Known actuators include a button, a switch, a lever, a slide, and the like. In use, the user may slide the output conduit 104 forward, i.e., towards the user, which activates the switch. As a result, the controller 406 may cause the motor 404 to rotate at a rotation rate in a rotational direction. In one embodiment, the controller 406 may be programmed to rotate the motor 404 so that an immediately subsequent receptacle 202 is moved into the heating chamber 204 and then automatically stop rotation thereafter. In another embodiment, the controller 406 may be programmed to continuously rotate the motor 404 until the user releases the switch. Accordingly, the user is able to control which one of the plurality of vaporizable substance receptacles 202 may be disposed within the heating chamber 204. Advantageously, the vapor viewing window 118 disposed on the output conduit 104 (see FIG. 1) may allow the user to view whether or not a particular receptacle 202 that is rotated into the user's view contains a substance (e.g., herbs). If, for example, the user is able to visually determine that a receptacle 202 within the heating chamber 204 does not include a sufficient amount of the vaporizable substance, the user may be prompted to continue rotating the receptacles 202 until the user is able to identify a filled receptacle 202. Although the present invention is described with reference to a rotational track-based assembly, it is understood that in other embodiments the vaporizer 100 may switch out the plurality of receptacles 202 in other ways, such as, for example, linear translation/movement of the receptacles 202 or other non-linear movement, including various planes, both horizontal and vertical. In addition, some embodiments may include manual mechanical translation or rotation of the plurality of receptacles 202, such as, for example, with a crank arm or lever.

Referring now primarily to FIGS. 6-8, the heating assembly 200 is illustrated in a perspective view, a plan view, and a fragmentary perspective view, respectively. The heating assembly 200, or, more particularly, an actively heated heating element 600, is thermally coupled to the airflow passage 300 (see FIG. 3) to reach the desired vaporizing temperature. The entire heating assembly 200, or one or more portions thereof, e.g. the heating element 600, may also be referred to as the "heat engine" or "heating engine" as it is this component that thermally charges the air to a proper vaporizing temperature. The term "thermally coupled" is defined as having a first and second object or matter in relative proximity such that heat is effectively exchanged from the first object to the referenced second object or matter. In one embodiment, the heating element 600 is a tungsten-based metallic alloy in the form of a coil that is disposed within the heating chamber 204 and at least partially disposed within the airflow passage 300 (see FIG. 3). In other embodiments, the heating element 600 is made from nickel-chrome, other types of metals, or metal-based composites that have a general low thermal resistivity and are generally safe to pass air through for human consumption. In further embodiments, the heating element 600 may be in the form of a plate or other shape, and may be disposed within the heating chamber 204 and/or in close proximity to the airflow passage 300 (see FIG. 3).

The heating element 600 may be energized by one or more batteries within the vaporizer 100. The heating assembly 200 may be designed to run on standard-sized batteries which includes lithium-ion based batteries. This is advantageous over prior known vaporizers that utilize fuel-based systems to heat the air to the vaporizing temperature because those fuel-based systems produce foul-tasting by-products and are generally loud and bring attention to the device. As such, the vaporizer 100 may be operable on standard portable batteries, with the possibility of recharging the batteries after continued use with an optional charging port (not shown). The batteries are also at least partially enclosed within the housing 102 (see FIG. 1) in a battery storage compartment (not shown).

Returning briefly to FIGS. 1-2, in one embodiment, a button 206, or other actuator, is provided on the housing 102 to activate the heating element 600. The user may depress the button 206 one or more times in order to cause the heating element 600 to be thermally charged. Power from the power supply causes the heating element 600 to reach a temperature sufficient to heat the vaporizable substance to a desired vaporizing temperature. In one embodiment, the vaporizer 100 is provided with a convection-based heating assembly that heats the air surrounding the vaporizable substance, rather than burning the substance itself. In other embodiments, the vaporizer 100 may utilize conduction-based heating, i.e. heating by direct contact of the herb with a heated material.

Referring again to FIGS. 6-8, in one embodiment, the heating assembly 200 includes a body 602 on which the heating elements 600 are disposed. In another embodiment, the body 602 is made of a conductive material, such as a metallic material or a conductive polymer material. In yet another embodiment, the body 602 may be made of other non-conductive materials or composites.

In a further embodiment, the body is formed as the gear 402. In other words, heating elements 600 that thermally charge the heating assembly 200 are disposed on the gear 402 such that the heating assembly 200 and the plurality of vaporizable substance receptacles 202 (not shown) rotate together as a result of the user activating the motor 404 (not shown). The exemplary embodiment depicted in FIGS. 6-8 show four heating elements 600, but, in other embodiments, there may be provided more or less than four heating elements 600. The body 602 may include a plurality of sidewalls 604. In one embodiment, the plurality of sidewalls 604 may define the receiving area 512, sized and shaped to receive the vaporizable substances receptacle 202 therein for rotating the track structure 500 (see FIG. 5).

FIG. 9 is a fragmentary, perspective view of the track structure 500 and heating assembly 200, illustrating the rotational heating chamber 204. As can be seen, only one of the heating elements 600 may be disposed within the heating chamber 204 at any given time. Rotation of the gear 402 also rotates the heating elements 600. In one embodiment, only the heating element 600 disposed within the heating chamber 204 may be thermally charged and once said heating element 600 is rotated out of the heating chamber 204, it is no longer actively heated. Stated another way, only one of the heating elements 600 on the gear 402 is actively heated at a time, the actively heated heating element 600 corresponding to the heating element 600 disposed within the heating chamber 204 and in direct fluid communication with the airflow passage 300 (see FIG. 3).

FIG. 10 is a fragmentary, perspective view of the track structure 500, heating assembly 200, and output conduit 104. More particularly, FIG. 10 illustrates placement of the transparent window 118 on the output conduit 104 directly above the heating chamber 204 (not shown) such that the heating chamber 204 is viewable by the user. Advantageously, users are able to enjoy a view of the creation of the vapors and rotation of the internal components within the vaporizer 100.

A novel and efficient multi-chamber vaporizer has been disclosed having a plurality of moveable vaporizable substance receptacles. Embodiments of the invention include a selectively rotatable track that supports the receptacles so that the receptacles can be rotated into and out of a heating chamber that heats the vaporizable substance. Embodiments of the invention provide for a gear that rotates the track so that each of the vaporizable substance receptacles can rotate into and out of the heating chamber. In a further embodiment, when the substance within the actively heated chamber is vaporized and the user desires to continue vaporizing, the user may engage an actuator that rotates the track and gear assembly so that the next vaporizable substance receptacle is rotated into the heating chamber for vaporizing. Embodiments of the invention also provide for transparent windows that allow a user to view rotation of the vaporizable substance receptacles within the vaporizer and also to view the heating assembly, as the active substance is boiled off into a cloud of vapors within the vaporizer housing.

What is claimed is:
1. A vaporizer comprising:
an elongated housing and a heating element disposed within the elongated housing, the elongated housing:
having a longitudinal length extending in an elongation direction from a first end of the elongated housing to a second opposing end of the elongated housing;
including an inner surface of the elongated housing defining a vaporizing cavity; and
an opening defined by one of the first end and the second opposing end of the elongated housing disposed to provide an entrance into the vaporizing cavity;
an actuator, at least a portion of the actuator disposed on an exterior surface of the elongated housing so as to be accessible by a user;
a rotatable support surface disposed within the vaporizing cavity;
a plurality of vaporizable substance receptacles, each of the plurality of vaporizable substance receptacles:
is disposed within the vaporizing cavity so as to be selectively rotatable via the actuator and the rotatable support surface along a rotation path within the vaporizing cavity;
includes an exterior surface, the exterior surface of each of the plurality of vaporizable substance receptacles being disposed to directly contact the rotatable support surface so as to permit the rotatable support surface to frictionally guide the plurality of vaporizable substance receptacles along the rotation path during a rotation via the actuator; and
is disposed a clearance distance from an adjacent one of the other ones of the plurality of vaporizable substance receptacles so as to be selectively, independently removable by the user away from the rotatable support surface and outside of the elongated housing for independently re-filling the separate receptacle body with a plant matter;
a mouth piece coupled to the one of the first end and the second opposing end of the elongated housing so as to overlap with the opening to form an airtight seal with the elongated housing at a coupling end of the mouth piece and an exit port at an open end of the mouth piece, the coupling end being opposite the open end; and
an airflow passage at least partially defined by the mouth piece, thermally coupled to the heating element and at least one of the plurality of vaporizable substance receptacles disposed proximate the mouth piece, and operably configured to, as a result of the user inhaling, deliver vapors from the vaporizing cavity through the opening and the exit port of the mouth piece and into a mouth of the user coupled to the mouth piece without expelling the vapors into the outside environment, the vapors being produced by the heating element heating a plant matter within the at least one of the plurality of vaporizable substance receptacles disposed proximate the mouth piece during the user inhaling.
2. The vaporizer in accordance with claim 1, wherein:
the plurality of vaporizable substance receptacles is rotatable along a circular path defined by a central axis.

3. The vaporizer in accordance with claim 2, wherein:
the rotatable support surface is formed as a track extending about the central axis so as to frictionally guide the plurality of vaporizable substance receptacles along the rotation path about the central axis.

4. The vaporizer in accordance with claim 1, further comprising:
a motor operably configured to rotate the plurality of vaporizable substance receptacles about a central axis at a rotation rate.

5. The vaporizer in accordance with claim 1, wherein:
the elongated housing is sized to include a maximum length extending from the first end to the second end of the elongated housing that is at most 6 inches.

6. The vaporizer in accordance with claim 1, further comprising:
a motor operably configured to selectively move the plurality of vaporizable substance receptacles.

7. The vaporizer in accordance with claim 1, wherein:
the heating element and the plurality of vaporizable substance receptacles are operably configured to rotate together.

8. The vaporizer in accordance with claim 1, further comprising:
a rotating gear operably configured to physically engage at least one of the plurality of vaporizable substance receptacles to rotate said vaporizable substance receptacle about a central axis.

9. The vaporizer in accordance with claim 1, wherein:
the elongated housing includes a transparent window through which at least one of the plurality of vaporizable substance receptacles is visible from the outside environment.

10. A portable hand-held vaporizer comprising:
a housing coupled to a mouthpiece defining an airflow passage for inhalation;
a heating element, the heating element having at least a portion thermally coupled to the airflow passage;
at least two vaporizable substance receptacles;
an actuator, at least a portion of the actuator disposed on an exterior surface the housing so as to be accessible by a user; and
a support surface, the actuator operably configured to allow a user to selectively cause the support surface to rotate about a central axis and the support surface supporting the at least two vaporizable substance receptacles thereon for rotation about the central axis, the heating element and the plurality of vaporizable substance receptacles operably configured to rotate together.

11. The vaporizer in accordance with claim 10, wherein:
the at least two vaporizable substance receptacles are disposed a separation distance from one another.

12. The vaporizer in accordance with claim 10, wherein:
the at least two vaporizable substance receptacles are of a conductive material.

13. The vaporizer in accordance with claim 10, further comprising:
a rotating gear configured to physically engage the at least two vaporizable substance receptacles to rotate said vaporizable substance receptacles about the central axis.

14. The vaporizer in accordance with claim 10, wherein:
the mouthpiece places the airflow passage in fluid communication with an outside environment, and at least one of the mouthpiece and the housing includes a transparent window through which at least a portion of the at least two vaporizable substance receptacles is visible from the outside environment.

15. The vaporizer in accordance with claim 10, further comprising:
a motor communicatively coupled to the actuator and operably configured to rotate the support surface and the at least two vaporizable substance receptacles about the central axis.

16. A vaporizer comprising:
a housing and a heating element disposed within the housing, the housing having:
a top wall;
a bottom wall opposite the top wall;
a sidewall including a first end and a second end opposite the first end and the sidewall separating the top wall from the bottom wall;
an inner surface of at least the top wall and the sidewall together defining a vaporizing cavity; and
an opening defined by one of the first end and the second end of the sidewall;
an actuator, at least a portion of the actuator disposed on an exterior surface the housing so as to be accessible by a user;
a rotatable support surface disposed within the vaporizing cavity;
a plurality of vaporizable substance receptacles substantially enclosed within the housing, each of the plurality of vaporizable substance receptacles:
is disposed within the vaporizing cavity so as to be selectively rotatable via the actuator along a rotation path within the vaporizing cavity;
includes an exterior surface, the exterior surface of each of the plurality of vaporizable substance receptacles being disposed to directly contact the rotatable support surface so as to permit the rotatable support surface to frictionally guide each of the plurality of vaporizable substance receptacles along the rotation path during the selective rotation via the actuator; and
is disposed a clearance distance from an adjacent one of the other ones of the plurality of vaporizable substance receptacles so as to be selectively, independently removable by the user away from the rotatable support surface and outside of the housing to independently re-fill the separate container body with a plant matter;
a mouth piece coupled to the one of the first end and the second end of the sidewall and overlapping with the opening defined by the sidewall; and
an airflow passage at least partially defined by the mouth piece, thermally coupled to the heating element and at least one of the plurality of vaporizable substance receptacles disposed proximate the mouth piece, and operably configured to, as a result of the user inhaling, deliver vapors from the vaporizing cavity through the opening and the mouth piece and into a mouth of the user coupled to the mouth piece without expelling the vapors into the outside environment, the vapors being produced by the heating element heating a plant matter within the at least one of the plurality of vaporizable substance receptacles disposed proximate the mouth piece during the user inhaling.

17. The vaporizer in accordance with claim 16, wherein:
the housing is sized to include a maximum length extending from the first end to the second end of the elongated housing that is at most 6 inches.

18. The vaporizer in accordance with claim 16, wherein:
the plurality of vaporizable substance receptacles is rotatable along a circular path defined by a central axis.

* * * * *